US00PP34051P3

(12) United States Plant Patent
Cohen

(10) Patent No.: US PP34,051 P3
(45) Date of Patent: Mar. 22, 2022

(54) ***CANNABIS* PLANT NAMED 'AVI-1'**

(50) Latin Name: ***Cannabis Sativa* L.**
Varietal Denomination: AVI-1

(71) Applicant: Tikun Olam Ltd., Tel Aviv (IL)

(72) Inventor: Ytzchak Cohen, Tel Aviv (IL)

(73) Assignee: Tikun Olam Ltd., Tel Aviv (IL)

( * ) Notice: Subject to any disclaimer, the term of this patent is extended or adjusted under 35 U.S.C. 154(b) by 0 days.

(21) Appl. No.: 16/974,161

(22) Filed: Oct. 27, 2020

(65) Prior Publication Data

US 2021/0051830 P1 Feb. 18, 2021

Related U.S. Application Data

(63) Continuation of application No. 16/602,269, filed on Sep. 3, 2019, now abandoned, which is a continuation of application No. 15/998,236, filed on Jun. 26, 2017, now abandoned, which is a continuation of application No. 14/757,039, filed on Nov. 12, 2015, now abandoned, which is a continuation of application No. 14/193,252, filed on Feb. 28, 2014, now abandoned.

(60) Provisional application No. 61/768,567, filed on Feb. 25, 2013.

(51) Int. Cl.
*A01H 5/00* (2018.01)
*A01H 6/28* (2018.01)

(52) U.S. Cl.
USPC ..... Plt./258
CPC ..... *A01H 6/28* (2018.05)

(58) Field of Classification Search
USPC ..... Plt./263.1, 258
See application file for complete search history.

(56) References Cited

PUBLICATIONS https://www.allbud.com/marijuana-strains/indica-dominant-hybrid/avi.dekel Mar. 17, 2021.*
Avidekel *Cannabis* Oil in Israeli autism study has 90% success rate Terry Smith. Jan. 27, 2019.*
Badiner Could pot stop breast cancer? 2012, retrieved on Feb. 28, 2019, retrieved from the Internet at https://www.salon.com/2012/11/26/could_pot_stop_breast_cancer/, 4 pp. (Year: 2012).
Bushwick. New, Low-THC Marijuana Should Relieve Pain Without the High 2012, retrieved on Feb. 14, 2019, retrieved from the Internet at http ://bl ogs. discovemagazi ne .com/80beats/2012/0 7 /06/new-low-thc-marijuana-should-relieve-pain-without-the-high/#. XGXWcPIKick, one page. (Year: 2012).
Kershener. Studying Marijuana and Its Loftier Purpose. The New York Times Safed Journal 2013, retrieved on Feb. 14, 2019, retrieved from the Internet at https://www .nytimes.com/2013/01/02/worid/middleeast/new-insights-on-marijuana-in-israel-where-its-illegal.html, 4 pp. (Year: 2013).
Trademark Electronic Search System AVIDEKEL, retrieved on Jul. 20, 2021, retrieved from the Internet at thttp://tmsearch.uspto.gov/bin/showfield?f=doc&state=4805:8o1jot.2.1, one page. (Year: 2021).
https://www.reuters.com/article/us-israel-marijuana/what-a-drag-israel-firm-grows-highless-marijuana-dUSBRE8620FU20120703, pp. 1-5).
www3.wipo.int/pluto/user/en/index.jsp PLUTO: Plant Variety Database, 2011 UPOV.
Trademark Electronic Search System AVIDEKEL, retrieved on Apr. 13, 2020, retrieved from the Internet at http ://tmsearch .uspto.gov/bin/showfield?=doc&state=4804:zdz106.2.1, one page. (Year: 2020).

* cited by examiner

*Primary Examiner* — Annette H Para
(74) *Attorney, Agent, or Firm* — Leasen Ellis LLP

(57) ABSTRACT

The disclosure relates to a new and distinct cultivar of *Cannabis Sativa* L. ssp. *indica* plant named 'AVI-1' characterized by a high amount of Cannabidiol (CBD) (16.3%) and a very low amount of Tetrahydrocannabinol (THC, 0.8%).

4 Drawing Sheets

Latin name of the genus and species of the plant claimed: *Cannabis Sativa* L.

Variety denomination: 'AVI-1'.

BACKGROUND

The disclosure is directed to a new and distinct cultivar of *Cannabis Sativa* plant named 'AVI-1', also known as 'Avidekel', characterized by a high amount of Cannabidiol (CBD) (16.3%) and a very low amount of Tetrahydrocannabinol (THC, 0.8%).

SUMMARY

Provided herein is a new and distinct *Cannabis Sativa* L. plant named 'AVI-1', characterized by a high amount of Cannabidiol (CBD) of greater than approximately 16% and a very low amount of Tetrahydrocannabinol (THC) of less than 1%, as illustrated and described herein.

DESCRIPTION

Figure 1:
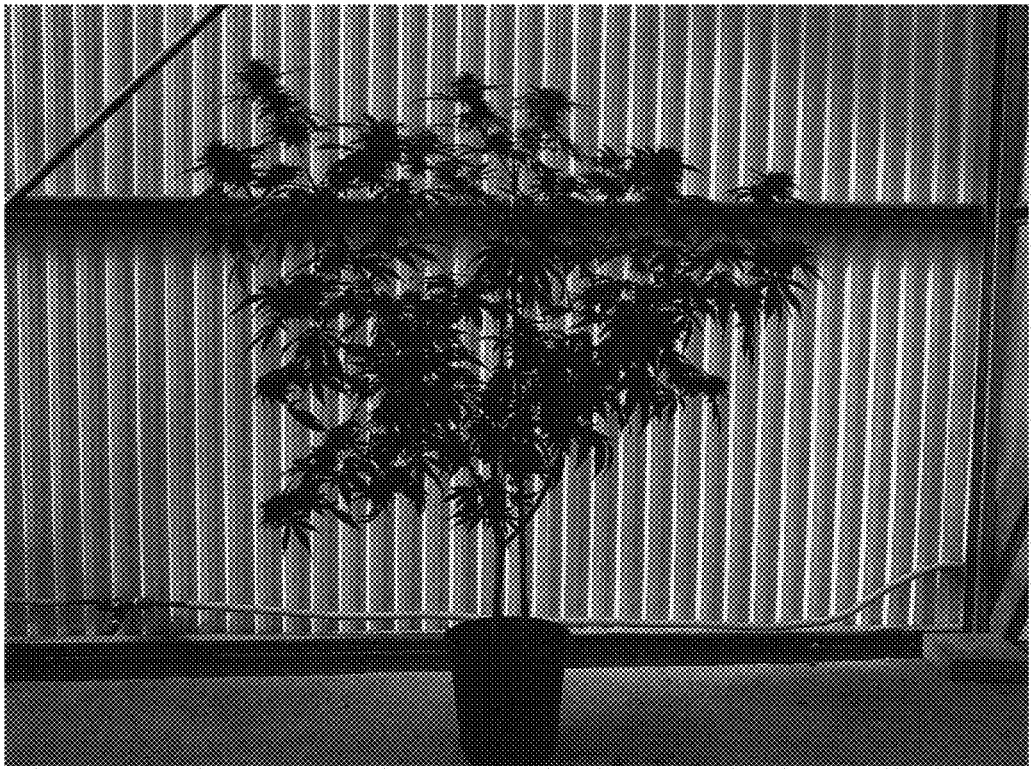
FIG. 1 illustrates a single fully grown plant of the variety.
Figure 2:
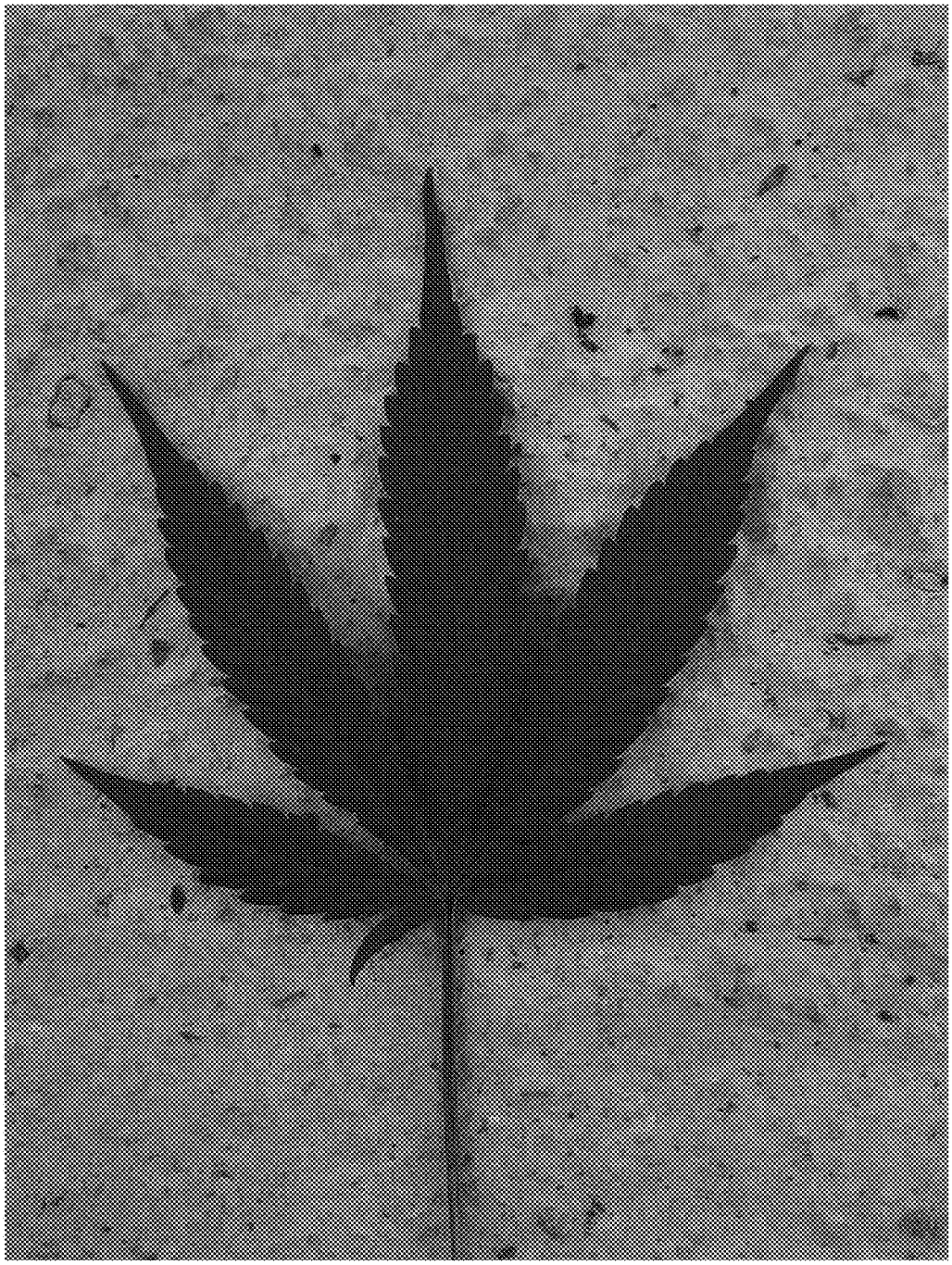
FIG. 2 illustrates a single leaf of the variety.
Figure 3:
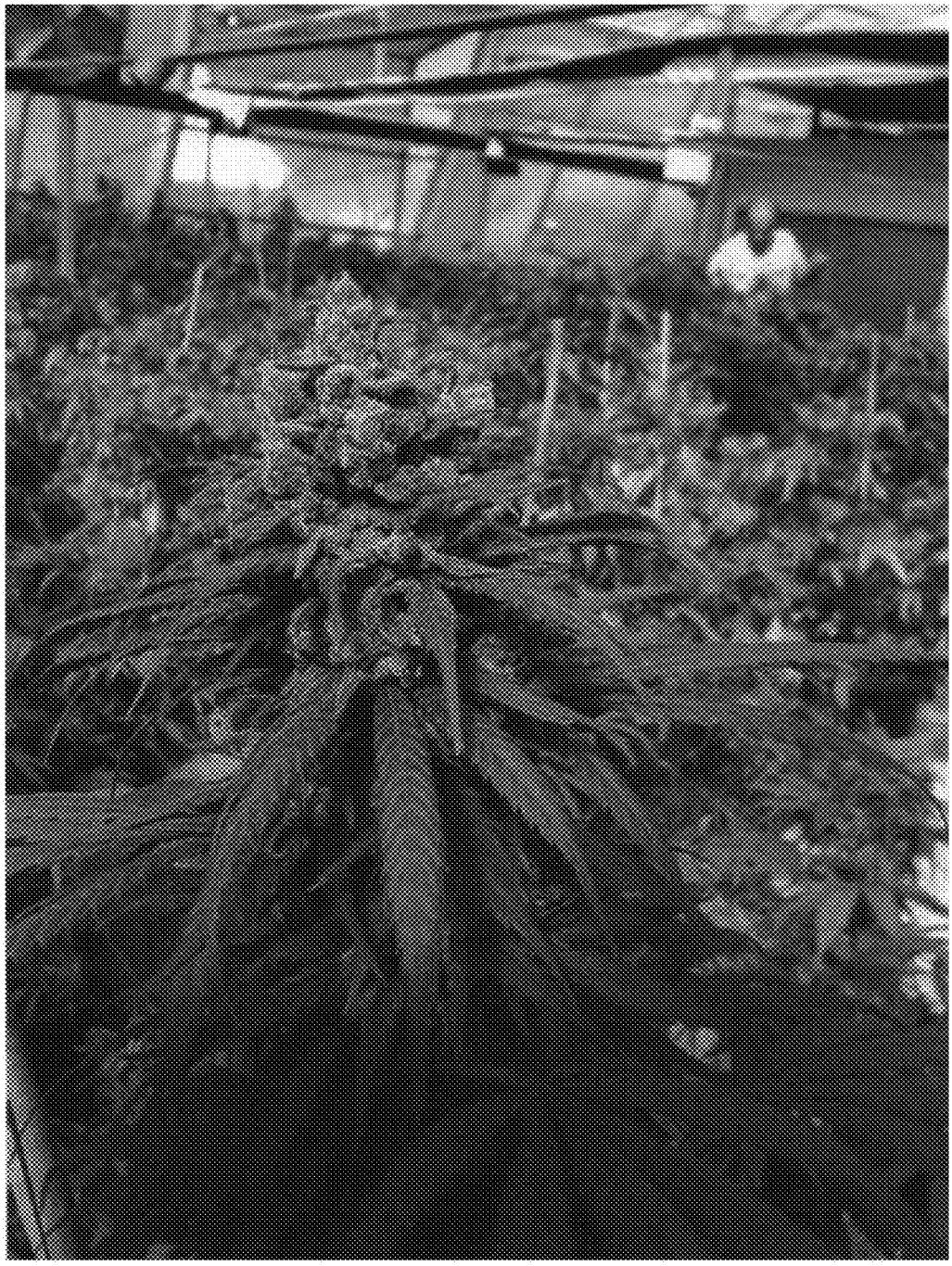
FIG. 3 illustrates a flowering plant in close-up.
Figure 4:
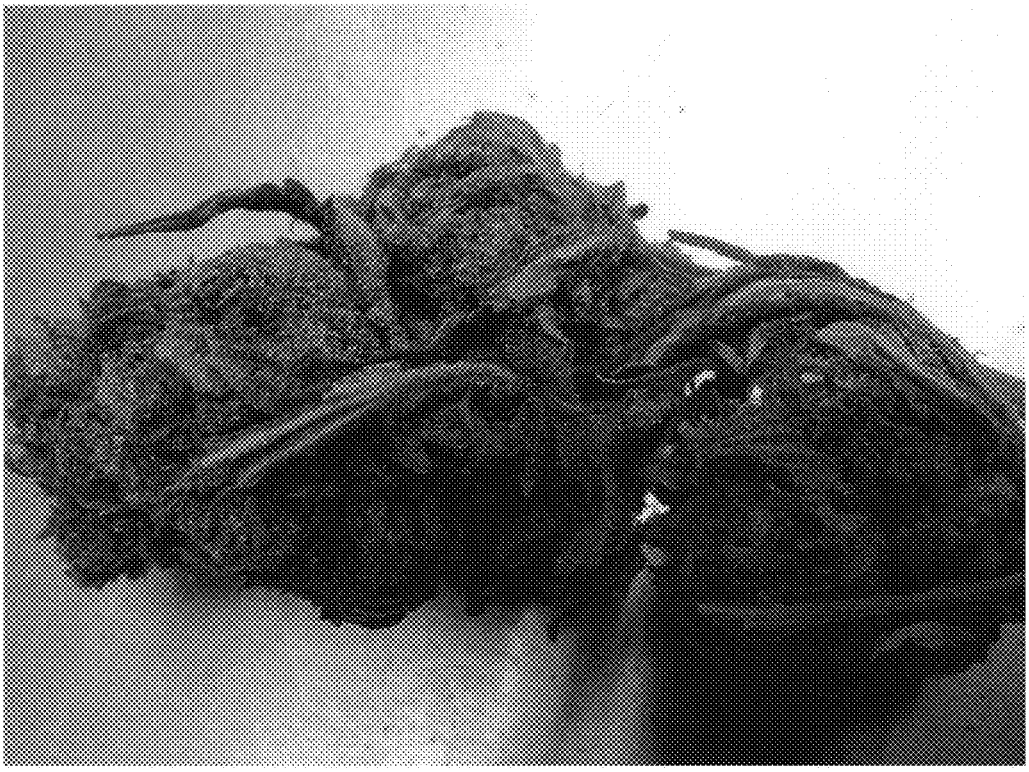
FIG. 4 illustrates a dried bud.

This invention relates to a new hybrid marijuana plant, *Cannabis sativa* L. named 'AVI-1'. The 'AVI-1' is a medicinal variety of marijuana notable for a high amount of Cannabidiol (CBD) (16.3%) and a very low amount of THC (0.8%). It is noted that CBD and THC content varied considerably between lots, different plants within a lot, and even difference between flowers form the same inflorescence. The extraction method and the HPLC procedure for determining THC and CBD content were well known in the art e.g., De Backera et al. (2009) Innovative development and validation of an HPLC/DAD method for the qualitative and quantitative determination of major cannabinoids in *Cannabis* plant material. J. of Chromatography B, 877: 4115-4124.

The present plant was developed over 3 years through selective breeding and asexual propagation using stem cutting of a selected feminized-plant at the inventor's farm, Farm 275, Birya 1380500, in Israel. The inventor grew, in one field, a mix of feminized, hermaphrodite and male plants that were high-CBD or low-THC. The plants flowered simultaneously. As a result, male flowers dispersed pollen, which transferred by wind and pollinated the female flowers, without human intervention. At the time plants reached maturation, the inventor had collected seeds as a bulk, and established B202 population. Subsequently, seeds, from the B202 population, were seeded and cultivated for the sake of selection. As soon the B202 plants were over 25 cm height, each plant was asexual propagated by using stem cutting methods. With cloned plants as backing, the original plants from B202 population sent to flowering. The variety 'AVI-1' derived directly from a single-plant selection, out of the flowering B202 population. Since the first selection, only asexual propagations were carried out. Through generations of asexual reproduction the unique features of this cultivar have proven to be stable and true to type.

'AVI-1' is an annual and dioecious plant where flowering are under elongated night condition. The size of an individual plant that develops from cutting, five weeks old in veg (18 h light) and 7-8 weeks into flowering (12 h light), can reach 60 cm in height.

The plant may be grown outside in a normal warm summer, including many locations below 50N and virtually all climates below 45N

PLANT

Exposed plant structure: The Plant is an annual, dioecious plant with bush-like stature. The natural height at 5 months old of indoor growth is ~130 cm. A detailed list of characteristics follows:

*Botanical classification.*—*Cannabis sativa* L.

*Parentage.*—Unknown.

*Propagation.*—Stem cuttings.

*Time to initiate roots in summer.*—

*Plant description.*—Annual, dioecious flowering shrub; multi-stemmed; freely branching; removal of the apical meristem of main stem enhances lateral branch development.

*Root description.*—Short taproot (less than 30 cm). Medium to fine, dense lateral roots; white in color, brownish when "potbound" (rootbound).

First year stems:

*Shape.*—Round. Fine pubescence.

*First year stem color.*—Young stem: 144C older stems: 144A (The Royal Horticultural Society Colour Chart).

*First year stem diameter.*—Is 4.5 cm.

*First year trunk diameter.*—Is 7.5 cm at the soil line.

*Stem strength.*—Lateral stems are strong but benefit from being staked during flowering.

*Internodes' length.*—6 cm in the lower half and 4cm in the upper half.

*Stem/canopy description.*—Erect, furrowed, hollow, tall, well branched with linear stipules. Stem's phyllotaxis is spiral with 144° between adjacent nodes. Canopy is densely branched at pubescent. Perpendicular section of young plant's stem is round, and hollow in the center. Perpendicular section of flowering plant's stem is crescent. Cover with fine trichomes (hair).

*Internode length.*—Up to 5 cm. Maximum internode length achieved during vigorous vegetative growth. The shape of naturally grown plant is pyramidal. It's formatted due to the apical dominance that allows the elongation of remote branches from the top of the main stem. The main stem has the following characteristics: the plant has an average canopy diameter of 40 cm, the main stem has a diameter of 9.9 mm, a short inter-node length, a shallow grove depth, absent of pith in cross section, the color is in the yellow green group (146-B or 146-C) with non-glandular, cystolithic hair (trichomes). The mean length of the stipule is 7.6 mm with a standard deviation of 0.5 mm. The mean width of the stipule is 0.6 mm with a standard deviation of 0.1 mm and a range of 0.5-0.7 mm. The color of the stipule is green group N137A, C. The shape of the stipule is acicular (needle).

*Branch strength.*—Strong.

Branch description.—Branches are short, densely branched with short, broad leaflets.

Foliage description:

*Leaf arrangement.*—Palmately compound (digitate) leaves with 5 or 7 leaflets on big fan leaves and on small fan leaves per leaf. The leaf arrangement is spiral phyllotaxis, 137.5° between adjacent leaves, counter-clockwise. At the shoot tip: 2:3 phyllotaxis of nascent leaves. For mature leaves, ⅖ phyllotaxis that draw five vertical rows of leaves along the stem and a 720° spiral between six adjacent leaves (five gaps). Texture (upper and lower surfaces). Upper surface scabrid with non-visible stiff hairs; lower surface more or less densely pubescent, covered with sessile glands.

*Venation pattern.*—Netlike, Palmately Compound), with serrated leaflets. Each serrated leaflets have a lateral vein extending to its tip from the central (primary) vein of the leaflet. From each lateral vein there is usually a single spur vein (sublateral vein) extending to the notch of each serration. Color of emerging foliage (upper surface). A cross between 144A and 144C (The Royal Horticultural Society Color Chart, 1995 Edition.) Leaf color are green (N137B) and yellow green group (146A). The leaves have a fragrance of weak lemony. The length of the leaf is 14.3 cm with a standard deviation of 1.2 cm. The average width of the leaf is 10.7 cm with a standard deviation of 1.4 cm. The length of the central leaflet is 11.1 cm with a standard deviation of 0.9 cm. The width of the central leaflet is 2.4 cm with a standard deviation of 0.1 cm. The mean blade/total length ratio is 70.9% with a standard deviation of 5.0% and a range of 62.8-75.8%. The mean blade width/length ratio is 22.8% with a 1.5% standard deviation of 1.5% and a range of 21.0-24.7%. The mean leaflets number is 5. The Adaxial side color is green group N137A, C and the abaxial side color is green group 137C.

*Petiole length*.—Average length of petiole is 29-33% of total length of the leave. The fan of the leaves is about 7 cm. More than 30% of the petioles are yellow green group 146C. The color anthocyanine is in the grey orange group GrOG 165-A. It has weak anthocyanin which is about 40%. Leaflets are lanceolate and have serrated margins. The middle leaflet is the longest and the wider. The bottom two leaflets are angled +90° with the center The leaflets are divided symmetrically by the central vain extending from the petiole to leaflet tip. Lateral veins extending from the central (primary) vein of the leaflet to the serration tips.

Flower bud description: Dried flower buds are deep dark green and highly resinous. Fragrance is weaker than similar varieties, having an earthy medicinal berry smell.

Flower description:

*Inflorescence is cone*.—Or head-like, dense cluster of false spikes with solitary flowers instead of cymes. Enclosed by glandular, beaked bracteole. Bracts and Calyxesare densely covered with trichomes. The bracts with the bracteoles are covered with multicellular glandular and sessile trichomes. For young flowers, the bract has an average length of 9 mm, width of 1 mm with a linear, slender, narrow shape in a yellow green color (146-B). The Bracteole has an average length of 10 mm, width of 4 mm, cordate shape that wraps the ovary (gynoecium) in a yellow green color (146-C). For mature flower, the bract has an average length of 10 mm, width of 1 mm, linear, slender and narrow shape in a yellow green color (149-C). The Bracteole has an average length of 10 mm, 5 mm width, acuminate, curled shape in a yellow green color (146-C). Flowers are often paired. Petals are absent.

*Spike length*.—Ranges between 5 cm and 3 cm.

*Pistils description*.—White, few, short, brown at maturation. For young flower, the pistil is monocarpous and has two stigmas. The average length of the pistil is 6 mm in a yellow green color (149-C). For mature flower, the pistil is monocarpous and has two stigmas. The average length of the pistil is 3.5 mm in a grey orange color (163-A).

*Dried flower colour*.—Dried flower buds are a deep, dark green (146-B and 146C). Pistil color is grey orange (167-A) with an average pistil length of 3 mm. The pedicel has an average length of 4 mm. The peduncle has a yellow green color (148-B).

*Flower size*.—About 1 cm in diameter and about 1.1 cm in height. Visually, a single female flower is green, sessile, bracteoles, fused calyx and two stigmata; flower length 8-10 mm, stigmata length 3-6 mm. The flowers are 100% female (feminized). Flower fragrance is medium pine, fruity and lemony.

*Flowering time*.—8 weeks: about 50 days from flipping to short day regime (12 h light+12 h dark).

Pistillate (female) inflorescence: Panicle like, congested cluster of sessile female flowers that create conical-cylinder inflorescence. The resins, that contain the cannabinoids, accumulate in the glandular glands. Stigmata colure of young flower yellow-green 145C, mature (week before harvest) Greyed orange group 165B. At maturation flower colure Green Group 138B. At maturation inflorescence length, can reach up to 20 cm. Dry flower, bud's leaf is 137B (Green group) in the adaxial side of the leaf and 137C in the abaxial. a medium to dark green, with orange 25B-stigmata.

Peduncles:

*Strength*.—Strong, but can bend horizontally from weight of flower buds.

*Texture*.—Moderately smooth, glabrous.

*Pedicels description*.—Short, scabrid with sessile glands and visible hairs.

The plant variety is similar to the Erez, also a *Cannabis indica* subspecies.

The inflorescence contains a high amount of Cannabidiol (CBD) (16.3%) and a very low amount of THC (0.8%). This enables patients to obtain the medicinal benefits of CBD, without the psychoactive effects of THC. As a comparison, Erez has about 18% THC and 0.7% CBD. The day to maturation for 'AVI-1' is about 56 days and for Erez is about 65 days.

There are no fruits in these plants. Resistance/susceptibility to plant disease and pest are not observed to date.

Prefers 'soft water'; consider filtering the tap water if it has an EC higher than 0.6

Light was provided at a power of 600W BPS; plant distance from light was 100-120 cm.

TABLE 1

| | |
|---|---|
| USDA Plants Growth Habit Code | Forb/herb |
| Vigor | 4.5/5 |
| Productivity | Good - 500 g/m2 indoor, 250-400 g/plant outdoor |
| Male flowering timing | 8 weeks |
| Branches | strong |
| Fruit | bloated |
| THC level | 0.8% |
| CBD level | 16.3% |

TABLE 2

| A crop was grown in a green house having the following times of growth cycle operations: | |
|---|---|
| date of cutting | 21 Apr. 2011 |
| date transferred to cones pot of 0.8 liter | 27 Apr. 2011 |
| Date of moved to pot of 11 liters | 23 May 2011 |
| Date of taking clones | 3 Jun. 2011 |
| Date - start to flower | 27 Jun. 2011 |
| Ending flowering | 23 Aug. 2011 |
| wet flowers (grams) | 524 |
| wet leaves (grams) | 250 |
| wet branches (grams) | 230.2 |
| dry flowers (grams) | 132.6 |
| Mothers | 1-1.5 meter |
| Pot size | 25 L |

Permits are required for growth of medical marijuana in certain states in the US and Israel.

The invention claimed is:

1. A new and distinct *Cannabis Sativa* L. plant named 'AVI-1', characterized by a high amount of Cannabidiol of greater than approximately 16% and a very low amount of THC of less than 1%, as illustrated and described herein.

* * * * *